United States Patent
Mälkki

(10) Patent No.: US 10,273,632 B2
(45) Date of Patent: Apr. 30, 2019

(54) METHOD FOR PRODUCTION AND USE OF NANOCELLULOSE AND ITS PRECURSORS

(71) Applicant: NANOREFIX OY, Helsinki (FI)

(72) Inventor: Yrjö Mälkki, Espoo (FI)

(73) Assignee: NANOREFIX OY, Helsinki (FI)

( * ) Notice: Subject to any disclaimer, the term of this patent is extended or adjusted under 35 U.S.C. 154(b) by 306 days.

(21) Appl. No.: 15/121,868

(22) PCT Filed: Mar. 11, 2015

(86) PCT No.: PCT/FI2015/000009
§ 371 (c)(1),
(2) Date: Aug. 26, 2016

(87) PCT Pub. No.: WO2015/136147
PCT Pub. Date: Sep. 17, 2015

(65) Prior Publication Data
US 2017/0067207 A1    Mar. 9, 2017

(30) Foreign Application Priority Data
Mar. 12, 2014 (FI) ...................................... 20140067

(51) Int. Cl.
*D21H 11/12* (2006.01)
*A61L 15/28* (2006.01)
*D21H 11/18* (2006.01)
*D21H 25/04* (2006.01)
*D21H 17/00* (2006.01)

(52) U.S. Cl.
CPC .............. *D21H 11/18* (2013.01); *A61L 15/28* (2013.01); *D21H 11/12* (2013.01); *D21H 17/005* (2013.01); *D21H 25/04* (2013.01); *A61L 2400/12* (2013.01)

(58) Field of Classification Search
None
See application file for complete search history.

(56) References Cited

U.S. PATENT DOCUMENTS

| 2014/0045785 A1 | 2/2014 | Herranen et al. |
| 2014/0179912 A1* | 6/2014 | Rasanen ................. C08B 15/02 536/56 |
| 2016/0289893 A1* | 10/2016 | Martin .................... B82Y 40/00 |

FOREIGN PATENT DOCUMENTS

| CN | 102899950 A | 1/2013 |
| CN | 103421203 A | 12/2013 |
| WO | WO-2007/001229 A1 | 1/2007 |
| WO | WO-2014/128354 A1 | 8/2014 |

OTHER PUBLICATIONS

Aaltonen et al., "The preparation of lignocellulosic aerogels from ionic liquid solutions," Carbohydrate Polymers, 75(1):125-129 (2009).
International Search Report and Written Opinion for Application No. PCT/FI2015/000009, dated Jun. 22, 2015.

* cited by examiner

*Primary Examiner* — Mary Lynn F Theisen
(74) *Attorney, Agent, or Firm* — Marshall, Gerstein & Borun LLP

(57) ABSTRACT

Objective of the method is a procedure for production of nanocellulose, where energy consumption and other costs of production are lower than in methods presented previously. It is based on separation of minute particles from cellulose or plant based ingredients by effects of light, thermal energy or water-soluble organic solvents. These particles act as precursors of nanocellulose. After separation they form in dry state aerosol, in liquid media a suspension, and combine to chains, microfibrils and secondarily formed fibrils, which form further networks with each other or with other fibers and fibrils. Applications are based on their action as reinforcing structure in composites, paper, cardboard, paints and other materials, on forming thin-layer films for electrical, electronic and medical applications, or on viscosity, surface and permeability properties.

15 Claims, No Drawings

METHOD FOR PRODUCTION AND USE OF NANOCELLULOSE AND ITS PRECURSORS

INTRODUCTION AND STATE OR ART

Purpose of this invention is a method for production and separation of nanocellulose and its precursors economically and with a small energy consumption, and for their use as such or without separation into pure state. The invention belongs to area of chemical technology.

In the following, the term nanocellulose is used to mean cellulose of particle size lower than one micrometer, precursors compounds or components formed in the biosynthesis of nanocellulose, such as elementary fibrils. These particles can be of varying size and shape. Nanocellulose has been shown to have several useful technical properties for applications on several branches of industries. Central properties deviating from conventional celluloses are high water binding, high viscosity at low concentrations, forming barrier layers for penetration of different materials, surface properties, high specific surface area, absorption and adsorption properties, ability to form aerogels, and high mechanical properties of microcrystalline cellulose. Potential applications have been presented, among others, for paper, cardboard, packaging, composite, electronic, medical, food and cosmetic industries.

Technologies presented for production of nanocellulose have been for their main part based on energy intensive mechanical milling, high pressure homogenization, use of strong acids or alkalies, cryogenic or other freezing, cryogenic milling, grafting of functional groups of atoms, enzymatic treatments, or their combinations. Using millings and homogenization, microfibrillar cellulose (MFC) is obtained. Its fibril diameter has in various preparations been 5 to 100 nanometres, and fibril length from tens of nanometres to several micrometres. The length to diameter ratio varies or cannot be calculated due to difficulties in measurements. With the acidic method, microcrystalline cellulose (MCC) is obtained, where the length to diameter ratio is from 2 to 10.

Operations for preparation are usually performed in water suspensions. Separation of the final product from diluted suspensions is difficult due to the small size of the particles, small difference in density as compared to water, water binding property, and viscosity properties. Due to costs in preparation and separation, cost of the final product has reached levels which has been preventive for intended economical uses. Development focused on production and applications has during the recent years been active and has led to several pilot and pre-commercial scale units. According to published data, the largest of these, started in 2011, has a capacity of one ton per day.

Production of microfibril cellulose is also possible to perform by separating it from naturally grown *Cladophora* algae (Ek et al., Cellulose powder from *Cladophora* sp. algae. Journal of Molecular. Recognition 11, 263-265, 1998; Mihranyan et al., Rheological properties of cellulose hydrogels prepared from *Cladophora* cellulose powder. Food Hydrocolloids 21, 267, 2007). Efforts to produce nanocellulose from genetically engineered blue green algae are still in experimental stage (https://cns.utexas.edu/news, 10 Apr. 2013).

Bacterial nanocellulose (BC) can be produced by various species of *Gluconacetobacter*, (earlier name *Acetobacter*), or related species. Cellulose material is produced in aerobic cultivations (WO 2005/003366 A1, Polytechnika Lodzka, 13 Jan. 2005) and can be further prepared and modified by several approaches (Fu et al., Present status and applications of bacterial cellulose-based materials for skin tissue repair. Materials Science and Engineering C 33, 2995-3000, 2013). Its principal applications have so far been in medical devices, especially for surgical implants and wound and burn healing. It is biocompatible, can act as scaffold in the growth of tissue and exhibit integration in the tissue. Production costs for such wound healing preparations, as estimated in 2007, were USD $0.02/cm^2$ (Czaja et al, The Future Prospects of Microbial Cellulose in Biomedical Applications. Biomacromolecules 8 (1) 1-12). Despite successful clinical results, as reviewed e.g. by Petersen and Gatenholm, (Bacterial cellulose-based materials and medical devices: current state and perspectives. Applied Microbiology and Biotechnology. 91, 1277-1286, 2011) use of this material has been very limited. Reasons are evidently in part high costs in cultivation, separation and handling of it, in part insufficient proofs of the reliability and controllability of the production technique.

Another application of BC studied in several research papers has been for composites. Mechanical properties of its microfibrils are found to be higher than those of nanocellulose from wood (review: Lee et al., On the use of nanocellulose as reinforcement in polymer matrix composites. Composites Science and Technology 105, 15-27, 2014). but production costs are still high to expect industrial applications for this purpose.

Tensile strength of crystalline nanocellulose has been found to be of similar magnitude than metallic aluminium, and its stiffness higher than of glass fibre. High mechanical properties have also been obtained for purified wood based microfibrils or bacterial microfibrils. Attention and expectations has been paid on their possibilities for use as reinforcing fibres in composites. Hundreds of research papers, made using the qualities obtained from the presently available experimental production, have been published and are reviewed by Lee et al. (*locus citatus*). In the majority of these, nanocellulose content in the composite has been below 20% of weight. A substantial reinforcing is achieved starting from a content of 30% upwards, but even at 95% content does not reach levels of purified preparations or levels calculated theoretically. Reasons found or suspected are low length to diameter ratio of nanoparticles, their agglomeration reducing effective length to diameter ratio, weak or uneven dispersion, incomplete wetting, weak adhesion to the binding material, porosity of the composite obtained, and multiple disturbing effects of residual water. Precondition for improving strength properties of composites is usually regarded to be a length to diameter ratio of above 50 or above 100.

By adding microfibrils to paper fibre mixture, an improving of mechanical properties and reduction of air permeability of paper has been achieved (WO 2013/072550 A2, UPM-Kymmene Corporation, 23 May 2013). The preparation used has been called fibril cellulose, and consisted of "a collection of isolated cellulose microfibrils or microfibril bundles derived from cellulosic material". It has been added to the fibre mixture during the wet stages of the process.

Preparation of aerogels, originally made from inorganic materials or carbon, has recently been able to produce also from cellulosic materials. Methods have been gel formation in water suspension, followed by exchange of solvent, and cryogenic or freeze drying (Fischer et al, Cellulose-based aerogels. Polymer 47, 7636-7645, 2006; Pääkkö et al., Long and entangled native cellulose I nanofibers allow flexible aerogels and hierarchically porous templates for functionalities. Soft Matter 4, 2492-2499, 2008; Heath and Tielemans, Cellulose nanowhisker aerogels. Green Chem. 12, 1448-1453, 2010). Reinforcing of the structure of aerogel has been found to be possible by binding with resorcinol formaldehyde resins (Tamon et al., Control of mesoporous structure of organic and carbon aerogels. Carbon 36, 1257-1262, 1998) or polyurethane (Fischer et al., *locus citatus*). Applications are based to low weight of volume, high porosity, high surface area in regard to weight or volume, and/or stability of the structure. Important applications presented are electrical and electronic industries, catalysators, heat and sound isolation, and medical industry.

From research in photonics it is known, that irradiation of light can move and transfer small sized particles. Regarding the amount of energy needed to release material from its site, only rough estimates exist, and the phenomenon has not knowingly been used preparatively or industrially.

METHOD

In the research now performed, it has been surprisingly found, that several lignocellulosic parts of agricultural crops already as such contain microfibrillar or microcrystalline cellulose, or materials which are apt to act as their precursors, and their separation or enriching is possible also more economically than by methods available presently. Material used in this research has been principally straw of cereal crops, various botanical parts of maize stover, and tissue paper, but methods used can be also applied to biomass from other non-wood plants and to products or side-streams of other cellulose producing industries, in limited scope also to other cellulose. The method is based on release from these materials of nano-sized particles, in dry state as aerosols, in liquid media as suspensions, by means of light energy, by controlled heating or by solvent treatment. After separating, the particles assimilate to chains, the chains orient with each other and combine forming microfibrils and secondary fibrils. Pretreatments, when needed, can be physical, dissolving, and enzymatic operations for disintegrating the cellular structure, for removal of inhibiting material layers, or for concentrating the part of material which can be exploited.

In microscopical studies it has now been surprisingly observed, that by focusing strong light on thin diameter cellulose fibrils they start to disintegrate to particles, sizes of which are on the resolution limit of optical microscopy. The particles are moving on their sites and can also separate from the plant tissue. After a delay, particles start to separate from the material. At the beginning, this separation can be observed as surface elevation, foam or aerosol. The particles move initially in the direction of the releasing light beam, later directed by local air flow and hinders for it, or by physical forces leading to adsorption or absorption.

The phenomenon can be weakly observed already caused by diffuse daylight, and depends on the intensity of the light. It is found to be affected by infrared, visible and ultraviolet light radiation, and also by thermal energy. This energy can also be produced from other electromagnetic energy sources such as microwave, radio frequency, or ohmic heating. Due to the known disintegration of cellulose by heat, temperature of treatment can be at the highest 180° C.

When the illumination continues and the local temperature elevates, residual moisture evaporates and is removed in the form of droplets or vapour. Small fragments of the material illuminated or heated can be separated simultaneously, follow along this particle flow, and are separated by gravity. Release of particles not observable by optical microscopy continues after this stage, and is observed as vibration of the macroscopic particles, diminution of the surface where light is focused, as accumulation of aerosol in its proximity, and as formation of new microfibrils on areas where particles are accumulated. The smallest particle type observable by optical microscopy is of club-like shape having a hydrophobic tail, of 30 to 100 nm in diameter, the other end being oval and hydrophilic. These particles are later called visible precursors. Additionally, ball-shaped particles or droplets of 0.5 to 3 µm in diameter are separated.

In microscopic studies it has been found, that these droplets have a multi-layered wall formed by the said visible precursors. In the innermost layer, visible precursors are oriented their hydrophilic ends inwards, in the next ones alternatively outward or inward. This structure prevents or retards evaporation of water, unless sufficient energy is available to generate vapour pressure to break this structure, releasing simultaneously said visible precursors. Precursors can also be separated from the ball shaped particles or water droplets or from the original lignocellulosic plant material by treatments with water-soluble organic solvents such as ethanol, methanol or acetone, based on removal of water, often more rapidly than by heating.

Without binding to any possible mechanism, the observations given in the paragraph above indicate, that the key mechanism of this method is removal of bound water from plant tissues or accumulations containing nanocellulose or its precursors. It is commonly known, that removal of the residual moisture, about 2%, from lignocellulosic materials is extremely difficult using conventional drying methods. Nanocellulose is commonly known to have high water retention capacity. Prolonged heating, infrared radiation, microwave radiation and water soluble organic solvents, have each a good ability to water removal and have now been found to induce separation of nano-sized particles. The weaker effect of ultraviolet radiation is evidently partly due to its known low penetration or to be caused by the effect of photons to induce mobility of small particles.

Microfibrils and secondarily formed fibrils continue to assimilate and grow during the input of external energy and even after it, duration depending on the amount energy fed, temperature, local concentration of nano-sized particles, and viscosity of the medium. After being ended, it can be restarted by restarting illumination, heat or solvent treatment.

Secondary fibrils can have diameters of 200 to 600 nm. The length of chains is often higher than 50 µm, the highest dimensions observed have been 5 mm. Accordingly, length to diameter ratios are thus at least 80.

Aerosol formed in dry state is in a fibrous material partly absorbed in pores, partly directed outside. Correspondingly, when the material to be treated is suspended in a liquid medium, particles released by heating or light radiation move and behave similarly, however depending on the viscosity of the medium. In treatments with water soluble organic solvents, nano-sized particles and subsequently microfibrils and secondary fibrils are for their main part separated or are formed instantaneously.

Ingredients found advantageous for the purpose are cellulose fibrils which are separated from fibres, are in damaged fibres, and/or have been treated by chemical or enzymatic means to remove layers of protecting materials. Rich sources of separate fibrils or fibrils which react strongly to effects of light, heat or solvents are, among others, straw cellulose, maize cobs, and recirculated paper or tissue paper containing it. Furthermore, transparent sheets appearing in strongly fibrillated cellulose are networks of nanofibrils. They are disintegrated in treatments according to this method to submicroscopic particles forming said precursors.

In selecting materials, hygienic and other purity requirements, including possible thermal or light influenced reactions of other components of the mixture, have to be regarded, depending of the application.

Precipitated thin layers can be amorphic and can remain in this state for months. Transforming to microfibril structures, clusters, secondary fibrils or networks is enhanced by moisture and/or additional energy or solvent treatments. Particles and clusters of nanocellulose and its precursors present in a feedstock, such as maize cob, recirculated fibre or tissue paper containing it can be separated to precursors and then accumulated to microfibrils, their clusters or thin transparent foils by light, thermal energy or by solvent treatments.

Suspensions containing particles of the same magnitude as in aerosols can be made in liquid media such as organic solvents or ingredients of plastics, rubbers or paints. Combining with other ingredients can be, for example, impregnating a pre-treated cellulosic material as such or combined with fibres or fibrils of other materials with such media and performing a heat or light treatment in one or several stages in this mixture. Nano-scaled particles are separated inside this mixture and form there secondary fibrils, their clusters or networks until it is prevented by hardening or other bonding of the medium. Aerosol which has been formed but not bound to microfibrils flows due to local pressure differences to pores or cracks of the material and converts gradually to fibrils or their network, whereby the bonds created reinforce the structure. These effects can be advanced by new heat or light treatments, even at lower temperatures than in previous treatments.

Preparation of an aerogel-like thin aerosol layer is most simply performed by treating a cellulose-based starting material by heat, light, other electromagnetic energy, and allowing the resulting aerosol to flow towards a selected surface, as such or after removal of water and fragments of the starting material by methods known as such. Fixing can be, for instance, by precipitation, adsorption or electrostatic means. For improving the stability of the layer it is advantageous to use a starting material from which finely divided fibrils can be separated and mixed in the aerosol flow, to support the structure. A tight aerosol layer can be converted to secondary fibrils or their clusters by using some of the said forms of energy.

Alternatively, aerosol is formed in a porous cellulosic material, extracted from it with a water-soluble organic solvent, and the suspension is applied to a selected surface where the solvent is evaporated. This allows an even and controllable thickness of the nano-sized material. Both of these alternatives can be used for production of thin nanocellulose layers to be used for electrical, electronic or medical applications.

Application of nanofibrils formed for reinforcing composites, paper or cardboard is most advantageous in combination of cellulosic or other macro-scale fibres. Microfibrils and secondary fibrils formed are found to crosslink cellulosic fibres and fibrils thus reinforcing the mechanical structure and also altering the permeability and surface properties. An advantage of this method is that nanocellulose is formed inside the material to be reinforced, whereby a too early agglomeration with other nano-sized particles is avoided.

In composites, the binding material is most often hydrophobic. When precursors are emitted, they have an immediate contact with this medium, and the hydrophobic tails ensure integration in it. As a result, also microfibrils and secondary fibrils formed have this immediate contact. No crevices separating fibrils from the binding medium have been observed by optical microscopy. Another advantage is the growth of these fibrils inside the binding medium to dimensions and length to diameter ratios which are needed for improving mechanical properties. Preconditions to allow or enhance the growth of secondary fibrils sufficiently are an applicable viscosity, temperature and time before hardening. Addition of nanocellulose containing ingredients to the composition has been found to elevate especially elastic modulus and impact strength. Due to the low length dimensions, an increase of tensile strength is not found, but expected to be achieved by including long fibres in the mixture to be reinforced.

Nanocellulose and its precursors prepared by this method are applicable for use in medical devices, for example for preparation of wound dressings and some surgical implants. In addition to the cost advantage as compared to bacterial nanocellulose it has the advantage to emit nano-sized particles to the wound, to support the growth of the healing tissue. This ability can be enhanced by activating before use a wound dressing containing this nanocellulose by an energy treatment of short duration, for example one minute, by microwave, ultraviolet or infrared treatment. The amount particles emitted during one day has been found to be less than 0.1 $mg/cm^2$.

Potential applications are for purposes and industries mentioned in the introduction. Procedures or principles of some typical applications are given in Examples, and subject to be optimized depending of the starting material and particular application, and further in the Claims.

EXAMPLES

Example 1

Enriching Nanocellulose and Precursors 8.8 g of paper produced from oat straw cellulose prepared according to U.S. Pat. No. 8,956,522 (Cerefi Ltd, 18 Apr. 2006) was pulped in 400 ml of demineralized water. 100 mg of citric acid was added for complexing potentially remaining divalent cations, whereby pH was lowered to 5.5. 0.5 ml of pectinase enzyme (Biotouch PL 300, AB Enzymes, Rajamäki, Finland) was added. The mixture was incubated at 50° C. for 90 minutes, and homogenized with a blade mixer. Subsequently the mixture was subjected to two freezing-thawing cycles to disintegrate the cellular structure. 1 ml of household tenside mixture (Nopa A/S, Denmark) was added, the mixture foamed by stirring, and dried in microwave oven by 700 W effect in six subsequent 30 sec periods. In the enriched product, clusters of visible precursors were microscopically discernible. The product, as such or omitting some of the steps given, as sheets or ground, can be used as an ingredient or intermediate, to be activated to nanocellulose or microfibrils within the product of an application, by energy sources or solvents given in the description.

Example 2

Microfibril Thin Layers on Solid Surfaces

A sample of the enriched nanoprecursor preparation according to Example 1 was illuminated with microscope lamp of 100 W, the light was focused to an area of 7 $mm^2$ After ca 30 seconds, disintegration producing aerosol started emitting nano-scaled particles. Flow of aerosol was directed to a glass plate placed 2 or 3 mm above the illuminated material. Thin film developed on the glass plate 3 mm above the illuminated cellulose sample had a homogenous and oriented network of microfibrils and was substantially free from solid fragments of the starting material, whereas such fragments were occasionally found on the glass plate 2 mm above the sample. Covering the glass plate with polyethene foil resulted collection of a similar network on this flexible material. This principle can be scaled up to larger batch or continuous productions for purposes of electrical and electronic industries and for production of medical devices.

Example 3

Effect on Mechanical and Surface Properties of Paper

From oat fibre cellulose prepared according to U.S. Pat. No. 8,956,502, paper sheets of 35 g/m$^2$ were prepared. When treated, they were in equilibrium with 38% air humidity. Test sheets were subjected to ultraviolet light (Omnilux R 80 75 W, omnilux-lamps.com), infrared light (Sylvania Infra-red 100 W, havells-sylvania.com) or microwave (700 W) irradiation, or immersion in 100% ethanol. Each treatment lasted for 60 seconds. Energy transferred at ultraviolet light or microwave treatments corresponded to 1.57 kWh/kg, and in infrared light treatment 2.09 kWh/kg of the paper. Under these conditions, treatments other than ultraviolet light resulted a similar development of microfibril network, cross-linking cellulosic fibres and fibrils of the paper. The effect of ethanol was the most rapid. After microwave treatment, elastic modulus of the paper, equilibrated to 50% air humidity, was measured. After one hour from treatment, no significant change from the starting value was observed. During 24 hours from the treatment, the elastic modulus elevated from initial value of 2.24 GPa to 15.34 GPa. With ultraviolet light, a thick aerosol was developed on and above the glossy surface adjacent to the light source, and was sedimenting slowly. After ultraviolet light treatment, no change in elastic modulus was found in 10 days. The difference has most probably been due to concentrating the effect on the surface, due to the lower penetration of the ultraviolet light, and by absence of any thermal effect, which with the other treatments had effected removal of residual moisture and consequently higher release of nano-scaled particles. The treatments effected a more dense fibrillar network, and a more smooth surface.

Example 4

Effect on Mechanical Properties of a Composite

From oat cellulose prepared according to U.S. Pat. No. 8,956,502, paper sheets of 102 g/m$^2$ were prepared and wet laminated in four layers in a vacuum sack equipment with Ashland Envirez polyester. Weight percentage of cellulose in the composite was 65%, curing time 12 hours at 80° C. Thickness of the resulting composite sheet was 1.1 mm. Flexural strength of the composite was 102 MPa, and flexural modulus 5.1 GPa. Corresponding values for polycondensed resin without fibre were 33.8 MPa and 3.0 GPa, respectively. Microscopic evaluation indicated that a part of the cellulosic material was converted to microfibrils and secondary fibrils during curing.

Example 5

Preparations for Burn and Wound Healing

Oat straw paper was prepared as described in U.S. Pat. No. 8,956,522, foam dried as described in Example 1, and activated by heating at 130° C. for 90 minutes. The product was tested for healing a bum wound of 70 mm in length, 5 mm broad, and 0.5 to 2 mm deep in an arm of a male patient. The product was placed on the wound when it started to exude liquid, and was removed after 12 hours. 24 days after the injury, microscopic study of surface samples of the healed skin revealed microfibrils mixed in the healed tissue indicating that aerosol from the product had integrated in it and supported the growth of the healing tissue. Within 6 months from the injury, no scar was formed, and also the surface pattern of the skin on the site of injury was similar to the skin nearby.

What is claimed is:

1. A method for production of nanocellulose, its precursors and concentrates, characterized by, that nanometer-sized particles are separated from fibrils of cellulosic material which is in dry or air-dry state, in organic solvents or in other hydrophobic liquid media, by removal of water by means of light, controlled heating or by water-soluble organic solvent.

2. A method according to claim 1, characterized by, that heat treatment is performed at temperatures not exceeding 180° C.

3. A method according to claim 1, characterized by, that heating is performed by feeding heat producing electromagnetic energy.

4. A method according to claim 1, characterized by, that the material to be treated consists of parts or constituents of non-woody plants.

5. A method according to claim 1, characterized by, that the material to be treated is recirculated cellulosic fibre or cellulosic material containing it.

6. A method according to claim 1, characterized by, that the cellulosic material is pretreated with hemicellulose or pectin decomposing enzymes.

7. A method according to claim 1, characterized by, that nanometre-scaled particles are separated in dry state as aerosol, and in a liquid medium as a suspension.

8. A method according to claim 1, characterized by, that nanometer-scaled particles are combined to each other forming chains, elementary fibrils, microfibrils, secondarily formed fibrils and networks of these.

9. A method according to claim 8, characterized by, that microfibrils, secondary fibrils or their network crosslink cellulosic fibres or fibrils.

10. A method according to claim 7, characterized by, that separation of nano-scaled particles and subsequent stages are performed in dry or air-dry cellulose material.

11. A method according to claim 7, characterized by, that separation of nano-scaled particles from cellulosic material and subsequent stages are performed when it is suspended in a hydrophobic liquid medium.

12. A method according to claim 11, characterized by, that the hydrophobic liquid medium consists of ingredients of composite or paint materials.

13. A method according claim 12, characterized by, that nano-scaled particles are bound with a binding material without any separating crack or crevice.

14. A method according to claim 9, characterized by, that it causes development of microfibril network improving mechanical and surface properties of paper.

15. A method according to claim 1, characterized by, that nanocellulose or its precursors are produced in a dressing material for treating wounds or burns and are emitted to the wound or burn surface from this material as such or after activatiation by light, controlled heating or water-soluble organic solvent.

* * * * *